(12) United States Patent
Nagai et al.

(10) Patent No.: US 11,372,007 B2
(45) Date of Patent: Jun. 28, 2022

(54) METHOD OF DETECTING BIOLOGICAL MATERIAL, AND CHEMILUMINESCENT INDICATOR USED THEREIN

(71) Applicant: Osaka University, Osaka (JP)

(72) Inventors: Takeharu Nagai, Osaka (JP); Yoshiyuki Arai, Osaka (JP)

(73) Assignee: Osaka University, Osaka (JP)

( * ) Notice: Subject to any disclaimer, the term of this patent is extended or adjusted under 35 U.S.C. 154(b) by 220 days.

(21) Appl. No.: 16/481,167

(22) PCT Filed: Jan. 26, 2018

(86) PCT No.: PCT/JP2018/002587
§ 371 (c)(1),
(2) Date: Jul. 26, 2019

(87) PCT Pub. No.: WO2018/139614
PCT Pub. Date: Aug. 2, 2018

(65) Prior Publication Data
US 2019/0353671 A1     Nov. 21, 2019

(30) Foreign Application Priority Data
Jan. 27, 2017    (JP) .............................. JP2017-013463

(51) Int. Cl.
G01N 33/72     (2006.01)
G01N 21/76     (2006.01)
G01N 21/78     (2006.01)
G01N 33/58     (2006.01)
G01N 33/68     (2006.01)

(52) U.S. Cl.
CPC ........... *G01N 33/728* (2013.01); *G01N 21/76* (2013.01); *G01N 21/78* (2013.01); *G01N 33/582* (2013.01); *G01N 33/68* (2013.01); *G01N 2800/085* (2013.01)

(58) Field of Classification Search
CPC ...... G01N 33/728; G01N 21/76; G01N 21/78; G01N 33/582; G01N 33/68; G01N 2800/085
See application file for complete search history.

(56) References Cited

U.S. PATENT DOCUMENTS

| 2006/0252110 A1* | 11/2006 | Gregory .................. C12Q 1/26 435/25 |
| 2014/0194307 A1 | 7/2014 | Hitko et al. |
| 2016/0009771 A1 | 1/2016 | Miyawaki et al. |
| 2016/0146794 A1 | 5/2016 | Johnsson et al. |
| 2017/0137473 A1 | 5/2017 | Gautier et al. |
| 2018/0087014 A1 | 3/2018 | Iwatani et al. |
| 2018/0201655 A1* | 7/2018 | Rodriguez ........... C07K 14/195 |

FOREIGN PATENT DOCUMENTS

| JP | 2016-500263 A | 1/2016 |
| WO | 02/068459 A2 | 9/2002 |
| WO | 2013/155553 A1 | 10/2013 |
| WO | 2014/093677 A1 | 6/2014 |
| WO | 2014/133158 A1 | 9/2014 |
| WO | 2015/007317 A1 | 1/2015 |
| WO | 2016/001437 A2 | 1/2016 |
| WO | 2016/159050 A1 | 10/2016 |

OTHER PUBLICATIONS

Pflger et al. "Bioluminescence resonance energy transfer (BRET) for the real-time detection of protein-protein interactions" Nature Protocols 2006 1:337 (Year: 2001).*
Tsuboi et al. "Recombinant protein (Luciferase-IgG binding domain) conjugated quantum dots for BRET-coupled near-infrared imaging of epidermal growth factor receptors" Biconjugate Chem. 2018 29: 1466-1474 (Year: 2018).*
Berlec (J. Veternary Diagnostic Investigation 2014 vol. 26: 521-526). (Year: 2014).*
England (Bioconjug Chem. 2016 vol. 18:1175-1187). (Year: 2016).*
Lin "mPlum-IFP 1.4 Fluorescent fusion protein may display Forster resonance energy transfer associated properties that can be used for near-infrared based reporter gene imaging" J. Biomecial Optics 2013 18: 126013 (Year: 2013).*
Eichhof "Oxygen-independent FbFP: fluorescent sentinel and oxygen sensor component in *Saccharomyes cerevisiae* and Candida Albicans" Fungal Genetics and Biology 2016 92:14 (Year: 2016).*
Potzkei Real-time determination of intracellular oxygen in bacteria using a genetically encoded FRET-based biosensor BMC Biology 2012 10:28 (Year: 2012).*
Mezzanotte "In vivo Molecular Bioluminescence imaging new tools and applications" Trends in Biotechnologyh 2017 35: 640 (Year: 2017).*
International Search Report issued in corresponding International Patent Application No. PCT/JP2018/002587 dated Mar. 20, 2018.
Kumagai et al., "A Bilirubin-Inducible Fluorescent Protein from Eel Muscle," Cell, 153:1602-1611 (2013).
Rodriguez et al., "A far-red fluorescent protein evolved from a cyanobacterial phycobiliprotein," Nature Methods, 13: 763-769 (2016).

(Continued)

*Primary Examiner* — Changhwa J Cheu
(74) *Attorney, Agent, or Firm* — Morgan, Lewis & Bockius LLP (57) ABSTRACT

Provided is a method of detecting a biological material, by which quantitative measurement can be performed easily. The method of detecting a biological material in a sample includes: mixing, with the sample, a fusion protein (C) in which a protein (A) capable of binding the biological material and a chemiluminescent protein (B) are fused together and a substrate for the chemiluminescent protein (B); and observing a luminescent signal from the sample, wherein the protein (A) and the protein (B) are linked in such a manner that resonance energy transfer can occur, the protein (A) is either a protein (A1) that can emit fluorescence in a state where the biological material is bound thereto or a protein (A2) capable of binding an autofluorescent molecule as the biological material, and the protein (B) can excite fluorescence or autofluorescence of the protein (A) with its luminescence energy.

20 Claims, 5 Drawing Sheets
Specification includes a Sequence Listing.

(56) References Cited

OTHER PUBLICATIONS

Shu et al., "Mammalian expression of infrared fluorescent proteins engineered from a bacterial phytochrome," Science, 324: 804-807 (2009).
Filonov et al., "Bright and stable near infa-red fluorescent protein for in vivo imaging," Nature Biotechnology, 29: 757-761 (2011).
Drepper et al., "Reporter proteins for in vivo fluorescence without oxygen," Nature Biotechnology, 25:443-445 (2007).
Chapman et al., "The photoreversible fluorescent protein iLOV outperforms GFP as a reporter of plant virus infection," PNAS 105: 20038-20043 (2008).
Shu et al., "A Genetically Encoded Tag for Correlated Light and Electron Microscopy of Intact Cells, Tissues, and Organisms," PLOS Biology, 9: e1001041 (2011).
Saito et al., "Luminescent proteins for high-speed single-cell and whole-body imaging," Nature Communications, 3: 1262 (2012).
Suzuki et al., "Five colour variants of bright luminescent protein for real-time multicolour bioimaging," Nature Communications, 7: 13718 (2016).
Ma et al., "Application of fluorescence resonance energy transfer in protein studies", Journal of Molecular Structure, 1077: 87-100 (2014).
Rumyantsev et al., "Near-infared bioluminescent proteins for two-color multimodal imaging", Scientific Reports, 6: 36588 (2016).
Extended European Search Report issued in corresponding European Patent Application No. 18744560.6 dated Oct. 7, 2019.

\* cited by examiner

METHOD OF DETECTING BIOLOGICAL MATERIAL, AND CHEMILUMINESCENT INDICATOR USED THEREIN

Sequence Listing Submission via EFS-Web

A computer readable text file, entitled "SequenceListing.txt," created on or about Jul. 26, 2019 with a file size of about 8 kb contains the sequence listing for this application and is hereby incorporated by reference in its entirety.

TECHNICAL FIELD

The present disclosure relates to a method of detecting a biological material and a chemiluminescent indicator used in the method.

BACKGROUND ART

Examples of a method of detecting a biological material in a sample include a method using a fluorescent protein. For example, Patent Document 1 proposes detecting unconjugated bilirubin, a biological material, using a UnaG protein or a variant thereof, each of which exhibits fluorescent properties upon binding unconjugated bilirubin.

Bilirubin is a degradation product of heme, which is a component of hemoglobin. Bilirubin is classified into unconjugated bilirubin (also referred to as "indirect bilirubin"), which is lipid soluble, and conjugated bilirubin (also referred to as "direct bilirubin"), which is water soluble. Unconjugated bilirubin is excreted into the blood and the urine when liver functions are reduced. A high level of indirect bilirubin can cause kernicterus (bilirubin encephalopathy).

Heretofore, a major method employed in bilirubin measurement is colorimetry represented by a diazo method. In blood tests, it is a common practice to calculate indirect bilirubin by measuring a total bilirubin (the total amount of direct bilirubin and indirect bilirubin) and direct bilirubin, and then subtracting the amount of the direct bilirubin from the total bilirubin.

CITATION LIST

Patent Documents

Patent Document 1: WO 2014/133158

DISCLOSURE OF INVENTION

Problem to be Solved by the Invention

In the case of detecting and quantifying a biological material using a fluorescent protein, such as UnaG, that binds the biological material, an excitation light source is required for observation. Moreover, since the method using such a fluorescent protein is based on single-wavelength excitation single-wavelength measurement, there are cases where quantitative measurement might be difficult.

With the foregoing in mind, in one aspect, the present disclosure provides a method of detecting a biological material and a chemiluminescent indicator, by which quantitative measurement can be performed easily.

Means for Solving Problem

In one or more embodiments, the present disclosure relates to a method of detecting a biological material in a sample (hereinafter also referred to as "the detection method of the present disclosure"), including:

mixing, with the sample, a fusion protein (C) in which a protein (A) capable of binding the biological material and a chemiluminescent protein (B) are fused together and a substrate for the chemiluminescent protein (B); and observing a luminescent signal from the sample, wherein the protein (A) and the protein (B) are linked so that resonance energy transfer can occur, the protein (A) is either a protein (A1) that can emit fluorescence in a state where the biological material is bound thereto or a protein (A2) capable of binding the biological material which is an autofluorescent molecule, and the protein (B) can excite fluorescence or autofluorescence of the protein (A) with luminescence energy of the protein (B).

In one or more other embodiments, the present disclosure relates to a chemiluminescent indicator containing:

a fusion protein (C) in which a protein (A) capable of binding a biological material and a chemiluminescent protein (B) are fused together, wherein the protein (A) and the protein (B) are linked so that resonance energy transfer can occur, the protein (A) is either a protein (A1) that can emit fluorescence in a state where the biological material is bound thereto or a protein (A2) capable of binding the biological material which is an autofluorescent molecule, and the protein (B) can excite fluorescence or autofluorescence of the protein (A) with luminescence energy of the protein (B).

In one or more other embodiments, the present disclosure relates to a vector or transformant that can express the fusion protein (C).

In one or more other embodiments, the present disclosure relates to a method including: determining the concentration of a biological material in a sample on the basis of luminescent signal data obtained by the detection method according to the present disclosure.

Effects of the Invention

In one aspect, the present disclosure can provide a method of detecting a biological material, by which quantitative measurement can be performed easily.

BRIEF DESCRIPTION OF DRAWINGS

FIGS. 6A and 6B show an example of the result of bilirubin measurement using a UnaG (CΔ0)-NLuc (NΔ1) fusion protein in Example 2.

FIGS. 7A and 7B show an example of the result of bilirubin measurement using a UnaG protein in Comparative Example 1.

DESCRIPTION OF THE INVENTION

The present disclosure is based on the finding that, in detection of a biological material, by fusing a chemiluminescent protein to a protein that emits fluorescence upon binding the biological material in such a manner that resonance energy transfer can occur, the necessity of using an excitation light source for observation is eliminated, and also, two wavelengths of measurement light can be used, and accordingly, quantification of the biological material can be performed easily.

In one or more embodiments, the detection method according to the present disclosure includes detecting a biological material in a sample using, as a chemiluminescent indicator, a fusion protein (C) in which a protein (A) capable of binding the biological material and a chemiluminescent protein (B) are fused together.

[Biological Material and Sample]

A detection target of the detection method according to the present disclosure may be a biological material in a biological sample. The biological sample is a sample containing the biological material derived from a living organism, and is preferably in a liquid state. Examples of such a biological sample include, but not particularly limited to, body fluid samples such as whole blood, serum, plasma, and urine. The biological sample in the present invention may be diluted and/or pretreated as necessary Needless to say, the detection method according to the present disclosure is also applicable to measurement of samples other than the above-described "biological sample". For example, the detection method is also applicable to a standard sample of a biological material to be detected, i.e., to a control sample used for the measurement. The biological material may be a biological material that binds to a protein (A) to be described below, and may be, for example, a low molecular weight compound in a living organism, a metabolite obtained by degradation, a nucleic acid, a sugar, a peptide, a protein, a cell, or a microorganism.

[Protein (A) Capable of Binding Biological Material]

In one or more embodiments, a "protein (A) capable of binding a biological material" according to the present disclosure may be a protein (A1) that can emit fluorescence in a state where a biological material is bound thereto or a protein (A2) capable of binding the biological material which is an autofluorescent molecule.

In one or more embodiments, the protein (A1) that can emit fluorescence in a state where a biological material is bound thereto may be a protein that is non-fluorescent when it is in the apo form and becomes fluorescent when it turns to the holo form upon binding a biological material that is a ligand. In one or more embodiments, the protein (A1) may be a UnaG protein. In one or more other embodiments, the protein (A1) may be smURFP, IFP, or iRFP.

A UnaG protein specifically binds to indirect bilirubin and emits green light when irradiated with cyan excitation light (Kumagai et al., Cell 2013, 153, 1602-1611). UnaG has very high binding ability to indirect bilirubin (dissociation constant=98 pM). For sequence information of UnaG, reference can be made to UniProtKB/Swiss-Prot: P0DM59.1 or GenBank: AB763906.1 (as of August 2016). By using a UnaG protein as the protein (A1), indirect bilirubin can be detected, for example.

smURFP is an abbreviation for small ultra red fluorescent protein, and refers to a protein that exhibits red fluorescence upon binding biliverdin, which is a metabolite of hemoglobin (Rodriguez et al., Nature Methods, 2016, 13, 763-769).

IFP is an abbreviation for infrared-fluorescent protein, and refers to a protein that exhibits red fluorescence upon binding biliverdin (Shu X, et al., Science 2009, 324 (5928), 804-8-7).

iRFP is an abbreviation for near-infrared fluorescent protein, and refers to a protein that exhibits red fluorescence upon binding biliverdin (Filonov G S, et al., Nat Biotech 2011, 29 (8), 757-761).

By using any of these smURFP, IFP, and iRFP as the protein (A1), biliverdin can be detected, for example.

The protein (A1) may be a variant of the UnaG protein or a variant of smURFP, IFP, or iRFP. The variant of the UnaG protein or the variant of smURFP, IFP, or iRFP may include a mutation(s) such as deletion, addition, and/or substitution to the extent that the variant can maintain its properties of being converted to the holo form and becoming fluorescent upon binding bilirubin or biliverdin as a ligand. The number of mutated amino acids is not particularly limited. In one or more embodiments, the number of mutated amino acids may be 1 to 4, 1 to 3, 1 to 2, or 1, or alternatively the amino acid sequence of the variant may have a sequence identity of at least 90% or more, 91% or more, 92% or more, 93% or more, 94% or more, 95% or more, 96% or more, 97% or more, 98% or more, 99% or more, or 99.5% or more. Non-limiting examples of the mutation include deletion of the fusion site (C-terminal or N-terminal) with the protein (B) in the fusion protein (C).

The protein (A2) capable of binding the biological material which is an autofluorescent molecule refers to a protein that becomes fluorescent upon binding the autofluorescent molecule. The autofluorescent molecule may be flavin mononucleotide (FMN). In one or more embodiments, the protein (A2) capable of binding the autofluorescent molecule (FMN) may be FbFP, an iLOV protein, or a mini-SOG protein.

FbFP is an abbreviation for flavin mononucleotide (FMN)-based fluorescent protein, and refers to a fluorescent protein derived from a blue-light receptor of bacteria (Drepper T., et al., Nat Biotech. 2007, 25(4) 443-445).

An iLOV protein is a protein with improved fluorescent properties obtained by modifying a fluorescent protein derived from a light, oxygen, or voltage-sensing (LOV) domain of a plant blue-light receptor phototropin (Chapman S., et al., PNAS 2008, 105 (50) 20038-43).

A mini-SOG protein is an abbreviation for mini singlet oxygen generator, and refers to a fluorescent protein derived from phototropin 2 in *Arabidopsis* (Shu X., et al., PLoS Biol. 2011, 9(4)).

The protein (A2) may be a variant that includes a mutation(s) such as deletion, addition, and/or substitution to the extent that the variant can bind the autofluorescent molecule. The number of mutated amino acids may be within the above-described ranges.

[Chemiluminescent Protein (B)]

The chemiluminescent protein (B) can excite fluorescence or autofluorescence of the protein (A) with its luminescence energy. According to the detection method of the present disclosure, in which the fusion protein (C) including the chemiluminescent protein (B) with such a configuration is used as a detection reagent, quantitative measurement of a biological material can be performed without using an excitation light source for observation. The chemiluminescent protein (B) may be a photoprotein (luciferase) that can serve as a resonance energy transfer donor and can excite fluorescence of the protein (A) at the time of resonance energy transfer. It is preferable that the protein (A) and the protein (B) exhibit different luminescent colors, because whether the detection target has been detected can be determined with reference to the luminescent color.

The resonance energy transfer is known as Förster resonance energy transfer (FRET) or bioluminescence resonance energy transfer (BRET). The protein (B) can be selected according to the absorption wavelength of the protein (A1) or the absorption wavelength of the autofluorescent molecule that binds to the protein (A2). Examples of the protein (B) include known photoproteins, such as firefly luciferase, aequorin, bacterial luciferase, and variants thereof.

When the protein (A) is UnaG, the protein (B) may be, in one or more embodiments, luciferase that uses a coelenterazine compound as a chemiluminescent substrate. In one or more embodiments, the luciferase may be NLuc.

The protein (B) may be a known variant of luciferase. The variant of luciferase may include a mutation(s) such as deletion, addition, and/or substitution to the extent that the variant can maintain its properties of emitting light upon binding luciferin. The number of mutated amino acids is not particularly limited. In one or more embodiments, the number of mutated amino acids may be 1 to 4, 1 to 3, 1 to 2, or 1, or alternatively, the amino acid sequence of the variant may have a sequence identity of at least 90% or more, 91% or more, 92% or more, 93% or more, 94% or more, 95% or more, 96% or more, 97% or more, 98% or more, 99% or more, or 99.5% or more. Non-limiting examples of the mutation include deletion of the fusion site (C-terminal or N-terminal) with the protein (A) in the fusion protein (C).

[Linker]

In the fusion protein (C), the protein (A) and the protein (B) may be bound via a linker. The linker may be selected so as to enhance the efficiency of resonance energy transfer from the protein (B) to the protein (A). In one or more embodiments, the length of the linker may be 1 to 10, 1 to 5, 2 to 4, or 2 to 3 amino acid residues.

When the protein (A) is UnaG, the linker may be GT, DD, GTG, GTGG, or the like in one or more embodiments. Among them, from the viewpoint of luminescence efficiency, DD, GTG, or GTGG is preferable and GTG is more preferable.

The order in which the protein (A) and the protein (B) are fused in the fusion protein (C) is not particularly limited, and either the protein (A) or the protein (B) may be on the N-terminal side of the fusion protein (C). In one or more embodiments, the fusion protein (C) may have a tag protein fused to the N-terminus or the C-terminus thereof.

According to the above-mentioned configuration of the fusion protein (C), the luminescent color of the protein (A) tends to be exhibited in the presence of both a biological material acting as a substrate for the protein (A) and luciferin acting as a substrate for the protein (B), and the luminescent color of the protein (B) tends to be exhibited more strongly as the amount of the biological material acting as the substrate for the protein (A) is reduced. Accordingly, the fusion protein (C) enables detection/measurement of the biological material.

[Detection Method]

Therefore, the detection method according to the present disclosure is a method of detecting a biological material in a sample, including:

mixing, with the sample, a fusion protein (C) in which a protein (A) capable of binding the biological material and a chemiluminescent protein (B) are fused together and a substrate for the chemiluminescent protein (B); and observing a luminescent signal from the sample, wherein the protein (A) and the protein (B) are linked so that resonance energy transfer can occur, the protein (A) is either a protein (A1) that can emit fluorescence in a state where the biological material is bound thereto or a protein (A2) capable of binding the biological material which is an autofluorescent molecule, and the protein (B) can excite fluorescence or autofluorescence of the protein (A) with its luminescence energy.

When a fusion protein (C) and a substrate for a protein (B) are added to a sample of interest, the sample emits light. Using this luminescent signal as an index, the presence or absence of a biological material that has bound to a protein (A) can be determined. Basically, the luminescent color of the protein (A) is exhibited in the presence of the biological material, and the luminescent color of the protein (B) is exhibited in the absence of the biological material.

In one or more embodiments, the detection method according to the present disclosure can be performed at room temperature or ambient temperature. In one or more embodiments, the time elapsing from the mixing of the fusion protein (C) with the substrate for the protein (B) until the observation may be around a few seconds to a few minutes, or around a few seconds to one minute. As the fusion protein (C) in the detection method according to the present disclosure, those described above can be used.

In one or more embodiments, in the detection method according to the present disclosure, the luminescent color of a sample changes in a manner dependent on the concentration of a biological material. As the concentration of the biological material increases, the luminescent color of the sample changes from the luminescent color of the protein (B) to the luminescent color of the protein (A). That is, the luminescence intensity ratio between the protein (A) and the protein (B) in a luminescent signal can be correlated with the concentration of the biological material.

Therefore, the detection method according to the present disclosure enables quantitative measurement of the concentration of the biological material on the basis of the luminescent signal, regardless of the amount of the sample. From the viewpoint of enabling the quantitative measurement, the molar concentration of the fusion protein (C) added to the sample is preferably within a range around the $K_d$ value.

In one or more embodiments, the detection method according to the present disclosure may include the step of quantitatively calculating the concentration of the biological material from the luminescent signal of the sample.

[Indicator]

In another aspect, the present disclosure relates to the fusion protein (C).

The fusion protein (C) can be used as a chemiluminescent indicator of the biological material. Therefore, in another aspect, the present disclosure relates to a chemiluminescent indicator containing: a fusion protein (C) in which a protein (A) capable of binding a biological material and a chemiluminescent protein (B) are fused together, wherein the protein (A) and the protein (B) are linked so that resonance energy transfer can occur, the protein (A) is either a protein (A1) that can emit fluorescence in a state where the biological material is bound thereto or a protein (A2) capable of binding the biological material which is an autofluorescent molecule, and the protein (B) can excite fluorescence or autofluorescence of the protein (A) with its luminescence energy.

The chemiluminescent indicator can be used in the detection method according to the present disclosure. Therefore, in another aspect, the present disclosure relates to the chemiluminescent indicator for use in the detection method according to the present disclosure, and to use thereof.

In one or more embodiments, the fusion protein (C) may be a recombinant protein produced using gene recombination technology or a protein synthesized by chemical synthesis. In one or more embodiments, the production of the recombinant protein using gene recombination technology may be performed by a method of producing a recombinant protein using a host transformed with an expression vector containing a gene encoding the fusion protein (C) or a method of producing a recombinant protein in a cell-free system. The fusion protein (C) may be purified by, for example, utilizing a tag protein.

[Nucleic Acid]

In one aspect, the present disclosure relates to a nucleic acid encoding the fusion protein (C) according to the present disclosure. In the present disclosure, examples of the nucleic acid include single-stranded or double-stranded DNAs selected from synthetic DNAs, cDNAs, genomic DNAs, and plasmid DNAs, and also, transcription products of these DNAs.

[Expression Cassette]

In one aspect, the present disclosure relates to an expression cassette that includes a nucleic acid encoding the fusion protein (C) according to the present disclosure. In the expression cassette, an expression regulatory sequence suitable for a host cell to be transfected with the expression cassette is operably linked to the nucleic acid. Examples of the expression regulatory sequence include promoters, enhancers, and transcription terminators. Other examples of the expression regulatory sequence include start codons, splicing signals in introns, and stop codons.

[Vector]

In one aspect, the present disclosure relates to a vector that can express the fusion protein (C) according to the present disclosure. In another aspect, the vector according to the present disclosure is, in one or more embodiments, an expression vector that includes a nucleic acid or expression cassette according to the present disclosure. As the vector according to the present disclosure, the type of expression vector suitable for a cell (host) in which the fusion protein (C) is intended to be expressed may be selected and used as appropriate. In one or more non-limiting embodiments, examples of a vector that can be used as the vector according to the present disclosure include plasmids, cosmids, YACS, virus (e.g., adenovirus, retrovirus, episomal EBV, and the like) vectors, and phage vectors.

[Transformant]

In one aspect, the present disclosure relates to a transformant that expresses the fusion protein (C) according to the present disclosure. In one or more embodiments, the present disclosure relates to a transformant that includes a nucleic acid or vector according to the present disclosure. In one or more embodiments, the transformant of the present disclosure can be produced by transfecting a host with a nucleic acid, expression cassette, or vector of the present disclosure. Examples of the host include animal cells, plant cells, insect cells, and microorganisms.

[Determination Method]

In another aspect, the present disclosure relates to a method of determining the concentration of a biological material in a sample, including: determining the concentration of the biological material in the sample on the basis of luminescent signal data obtained by the detection method according to the present disclosure.

As described above, the luminescence intensity ratio between the proteins (A) and (B) in the luminescent signal obtained by the detection method according to the present disclosure can change in a manner dependent on the concentration of the biological material. Therefore, the concentration of the biological material can be determined from the information on the fusion protein (C) used for the detection and the luminescent signal.

The luminescent signal data can be easily captured and transmitted/received using a color detector such as a color camera of a mobile terminal (smartphone or the like). Accordingly, the concentration of the biological material can be grasped easily.

The present disclosure further relates to one or more non-limiting embodiments to be described below.

[1] A method of detecting a biological material in a sample, the method including:

mixing, with the sample, a fusion protein (C) in which a protein (A) capable of binding the biological material and a chemiluminescent protein (B) are fused together and a substrate for the chemiluminescent protein (B); and observing a luminescent signal from the sample, wherein the protein (A) and the protein (B) are linked in such a manner that luminescence energy transfer can occur, the protein (A) is either a protein (A1) that can emit fluorescence in a state where the biological material is bound thereto or a protein (A2) capable of binding an autofluorescent molecule as the biological material, and the protein (B) can excite fluorescence or autofluorescence of the protein (A) with its luminescence energy.

[2] The method according to [1], wherein the protein (A1) is a UnaG protein or a variant thereof, each of which can emit fluorescence in a state where bilirubin is bound thereto, and the biological material to be detected is bilirubin.

[3] The method according to [1], wherein the protein (A1) is a protein selected from the group consisting of IFP, iRFP, smURFP, and variants thereof, each of which can emit fluorescence in a state where biliverdin is bound thereto, and the biological material to be detected is biliverdin.

[4] The method according to any one of [1] to [3], wherein the protein (A2) is a protein selected from the group consisting of FbFP, iLOV proteins, mini-SOG proteins, and variants thereof, each capable of binding flavin mononucleotide, and the biological material to be detected is flavin mononucleotide.

[5] A chemiluminescent indicator comprising:

a fusion protein (C) in which a protein (A) capable of binding a biological material and a chemiluminescent protein (B) are fused together, wherein the protein (A) and the protein (B) are linked in such a manner that resonance energy transfer can occur, the protein (A) is either a protein (A1) that can emit fluorescence in a state where the biological material is bound thereto or a protein (A2) capable of binding an autofluorescent molecule as the biological material, and the protein (B) can excite fluorescence or autofluorescence of the protein (A) with its luminescence energy.

[6] The chemiluminescent indicator according to [5], for use in the method according to any one of any one of [1] to [4].

[7] A vector or transformant that can express the fusion protein (C) defined in any one of [1] to [4].

[8] A method of determining the concentration of a biological material in a sample, the method including:

determining the concentration of the biological material in the sample on the basis of luminescent signal data obtained by the method according to any one of [1] to [4].

Hereinafter, the present disclosure will be described in further detail by way of examples. However, these examples are merely illustrative, and the present disclosure is not limited to these examples.

EXAMPLES

Example 1

1. Gene Construction of Fusion Proteins (Chemiluminescent Indicators)

C-terminal deletion mutants of a wild-type UnaG were amplified using the following primers with a BamHI restriction enzyme site added to the N-terminal primer and a KpnI restriction enzyme site added to the C-terminal primers.

```
Forward primer:
                                      (SEQ ID NO: 1)
CGCGGATCCGGGTGGTTCTGGTATGG Reverse primer 0:
                                      (SEQ ID NO: 2)
(CΔ0) GCTGGTACCTTCCGTCGCCCTCCG Reverse primer 1:
                                      (SEQ ID NO: 3)
(CΔ1) GCTGGTACCCGTCGCCCTCCGGTA Reverse primer 2:
                                      (SEQ ID NO: 4)
(CΔ2) GCTGGTACCCGCCCTCCGGTAGCT Reverse primer 3:
                                      (SEQ ID NO: 5)
(CΔ3) GCTGGTACCCCTCCGGTAGCTGCG Reverse primer 4:
                                      (SEQ ID NO: 6)
(CΔ4) GCTGGTACCCCGGTAGCTGCGCAC
```

N-terminal deletion mutants of a wild-type NLuc were amplified using the following primers with a KpnI restriction enzyme site added to the N-terminal primers and an EcoRI restriction enzyme site added to the C-terminal primer.

```
Forward primer 1:
                                      (SEQ ID NO: 7)
(NΔ1) GCCGGTACCGTCTTCACACTCGAAGATTTCG Forward primer 2:
                                      (SEQ ID NO: 8)
(NΔ4) GCCGGTACCCTCGAAGATTTCGTTGGGGAC Forward primer 3:
                                      (SEQ ID NO: 9)
(NΔ5) GCCGGTACCGAAGATTTCGTTGGGGACTGGC Reverse primer:
                                      (SEQ ID NO: 10)
ATGAATTCTTACGCCAGAATGCGTTCGCACAG
```

DNA fragments amplified by polymerase chain reaction (PCR) were extracted using a phenol-chloroform extraction method. The DNA fragments of UnaG were treated with restriction enzymes BamHI and KpnI. The DNA fragments of NLuc were treated with restriction enzymes KpnI and EcoRI. After agarose gel electrophoresis, bands were excised from the gel and purified (QIAEX2, QIAGEN). pRSET$_B$ vectors that had been treated with restriction enzymes BamHI and EcoRI were ligated to the thus-purified respective fragments, which were then transformed into the JM109 (DE3) strains. Thereafter, the JM109 (DE3) strains were cultured at 37° C. overnight on LB agar media prepared in 10-cm dishes.

2. Screening

The agar media in which colonies were formed were placed at room temperature. 4 mL of a solution containing bilirubin at a final concentration of 10 μM was added to 1% low-melting agarose gel that had been cooled to near room temperature, and the resultant mixture was poured onto the agar media and allowed to solidify at room temperature. Subsequently, a 10 μM Coelenterazine-h solution was poured onto the gel. Immediately after adding the solution, color images of the colonies were taken with a single-lens reflex camera (Sony α7) placed in a dark box. Ratio images were created from green channel (luminescence of UnaG) images and blue channel (luminescence of NLuc) images of the RGB images, and the colonies exhibited high ratio values were picked up. Next, the colonies thus picked up were cultured in LB media containing 10 μM bilirubin and 100 μg/mL Ampicillin at 23° C. for 60 hours on a 96-well plate. 10 μM coelenterazine was added to the culture solutions, and chemiluminescence spectra were measured using a spectrophotofluorometer (FV7000) or a plate reader. The chemiluminescence spectra were normalized at a wavelength of 450 nm, and screening was performed on the basis of a relative value (ratio value) at a wavelength of 525 nm.

Figure 1:
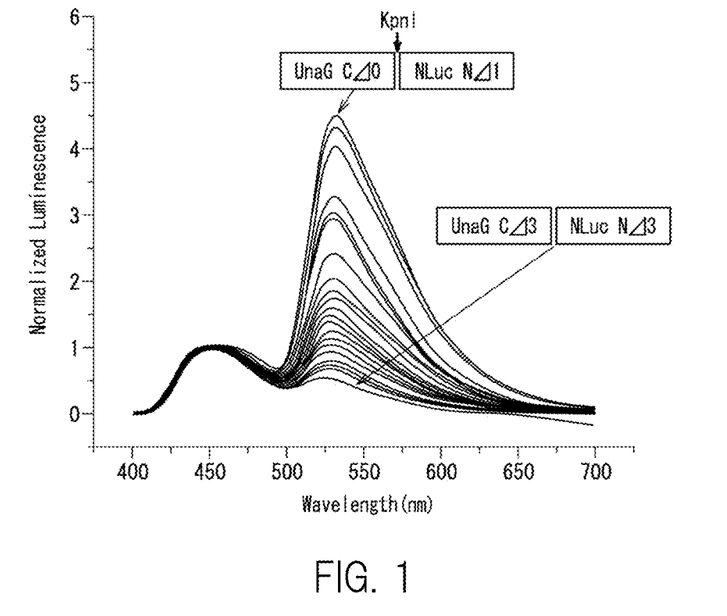
FIG. 1 shows chemiluminescence spectra of various UnaG-NLuc fusion proteins with C-terminal/N-terminal deletion mutations. UnaG (CΔ0)+NLuc (NΔ1) exhibited the highest FRET efficiency

As a result of screening proteins obtained by fusing the C-terminal deletion mutants of UnaG and the N-terminal deletion mutants of NLuc at the KpnI site, the combination of UnaG (CΔ0) and NLuc (NΔ1) (hereinafter referred to as "UnaG (CΔ0)-NLuc (NΔ1) fusion protein") exhibited the highest Førster resonance energy transfer (FRET) efficiency (FIG. 1). The base sequence of this UnaG (CΔ0)-NLuc (NΔ1) fusion protein is represented by SEQ ID NO: 11, and the amino acid sequence of the same is represented by SEQ ID NO: 12.

3. Optimization of Linker Sequence in Fusion Protein

Two residues (GT) constituting a sequence at the junction (a linker sequence) of UnaG and NLuc, were substituted with random sequences by inverse PCR. The following primers were used.

```
Forward primer:
                             (SEQ ID NO: 13)
NNKNNKGTCTTCACACTCGAAGATTTC Reverse primer:
                             (SEQ ID NO: 14)
TTCCGTCGCCCTCCGGTAGCTG
```

The full-length sequences including vector sequences were amplified, and then treated with a restriction enzyme Dpnl to treat template plasmids. After ligation, they were transformed into the JM109 (DE3) strains, which were then cultured at 37° C. overnight on LB agar media prepared in 10-cm dishes. Colonies expressed were subjected to screening in the manner described in the above item 2.

4. Insertion of Linker Sequences into Fusion Proteins

Linker sequences were inserted after the sequence (GT) at the junction of UnaG and NLuc by inverse PCR. The following primers were used.

```
Forward primer (G):
                             (SEQ ID NO: 15)
GGCGTCTTCACACTCGAAGATTTC Forward primer (GG):
                             (SEQ ID NO: 16)
GGCGGCGTCTTCACACTCGAAGATTTC Forward primer (GGS):
                             (SEQ ID NO: 17)
GGCGGGCAGCGTCTTCACACTCGAAGATTTC Reverse primer:
                             (SEQ ID NO: 18)
GGTACCTTCCGTCGCCCTC
```

The full-length sequences including the vector sequences were amplified by PCR, and then treated with a restriction enzyme Dpnl to treat template plasmids. After ligation, they were transformed into the JM109 (DE3) strains, which were then cultured at 37° C. overnight on LB agar media prepared in 10-cm dishes. Colonies expressed were subjected to screening in the manner described in the above item 2.

Figure 2:
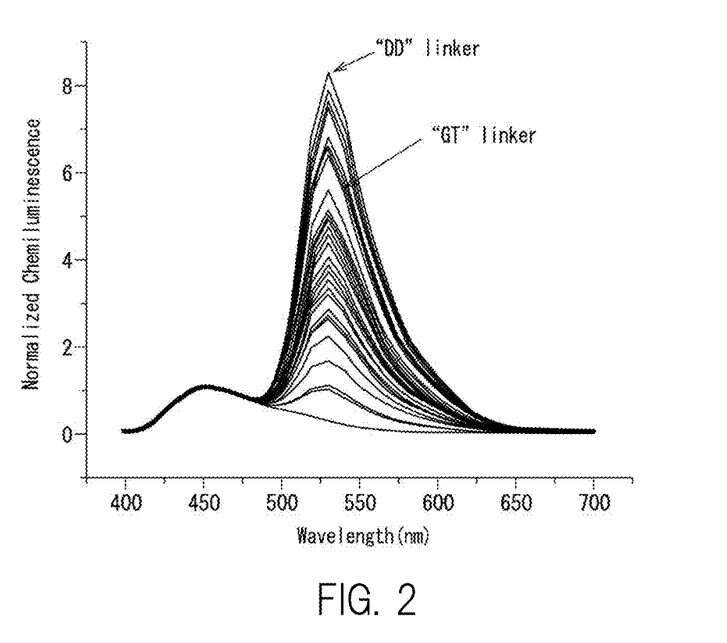
FIG. 2 shows chemiluminescence spectra obtained when various mutations were inserted to a linker sequence. As compared with a wild-type chemiluminescent bilirubin indicator with the linker sequence (GT), a mutant obtained by substituting the sequence (GT) with a DD sequence exhibited the largest change in FRET efficiency.

As a result of the linker sequence optimization by the insertion of random mutations, the (DD) sequence exhibited a large change in FRET efficiency as compared with the wild-type linker sequence (GT) (FIG. 2). Furthermore, examination on the FRET efficiencies of the chemiluminescent bilirubin indicators to which the flexible linkers had been added revealed that the chemiluminescent bilirubin indicator with the (GTG) sequence exhibited the highest FRET efficiency.

5. Purification of Protein

The JM109 (DE3) strain transformed with the UnaG (CΔ0)-NLuc (NΔ1) fusion protein was cultured at 23° C. for 60 hours in 200 mL of LB medium containing 100 μg/mL Carvenisillin solution. After harvesting, the *E. coli* cells were disrupted by the French press method and purified by affinity chromatography using a Ni-NTA column (QIAGEN). Furthermore, in order to remove excess imidazole, a gel filtration column (PD-10, GE HealthCare) was used. The protein concentration was measured by the Bradford method.

6. Preparation of Lyophilized Samples

500 μL of the purified UnaG (CΔ0)-NLuc (NΔ1) fusion protein was added to a 15-mL Falcon tube and frozen with liquid nitrogen. Thereafter, a powder of the protein solution was obtained by a lyophilizer. The powder was stored at room temperature.

Figure 3:
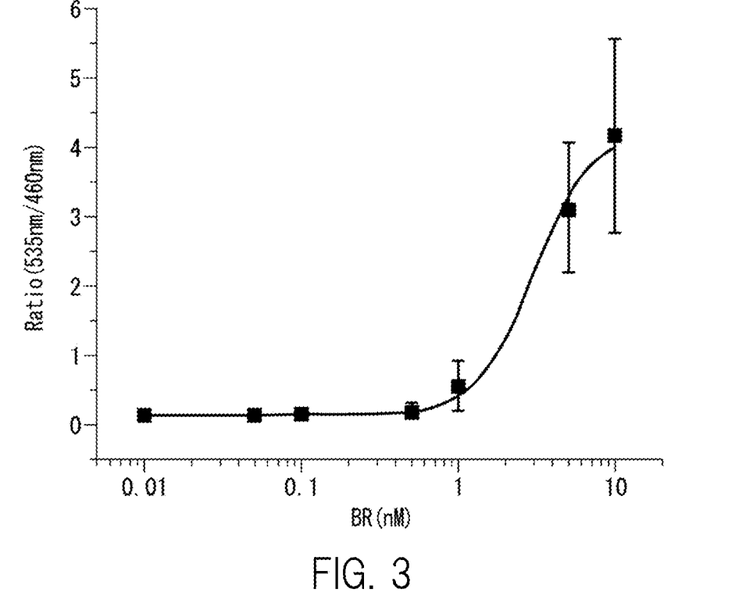
FIG. 3 shows a titration curve of the wild-type chemiluminescent bilirubin indicator. Mean values of measured values obtained by three independent measurements were plotted, and then fitted as per the Hill equation. The $R_d$ value was 3.05 nM.

7. Measurement of Titration Curve 0.01 nM, 0.05 nM, 0.1 nM, 0.5 nM, 1 nM, 2.5 nM, 5 nM, or 10 nM bilirubin (BR) solution and Coelenterazine-h at a final concentration of 5 μM were mixed with the UnaG (CΔ0)-NLuc(NΔ1) fusion protein at a final concentration of 5 nM, and luminescence spectra were measured using a multichannel spectroscope (PMA-12, manufactured by Hamamatsu Photonics K.K.) or a plate reader. FIG. 3 shows an example of the result obtained. Mean values of measured values obtained by three independent measurements were plotted, and then fitted as per the Hill equation. The $K_d$ value was 3.05 nM.

Figure 4:
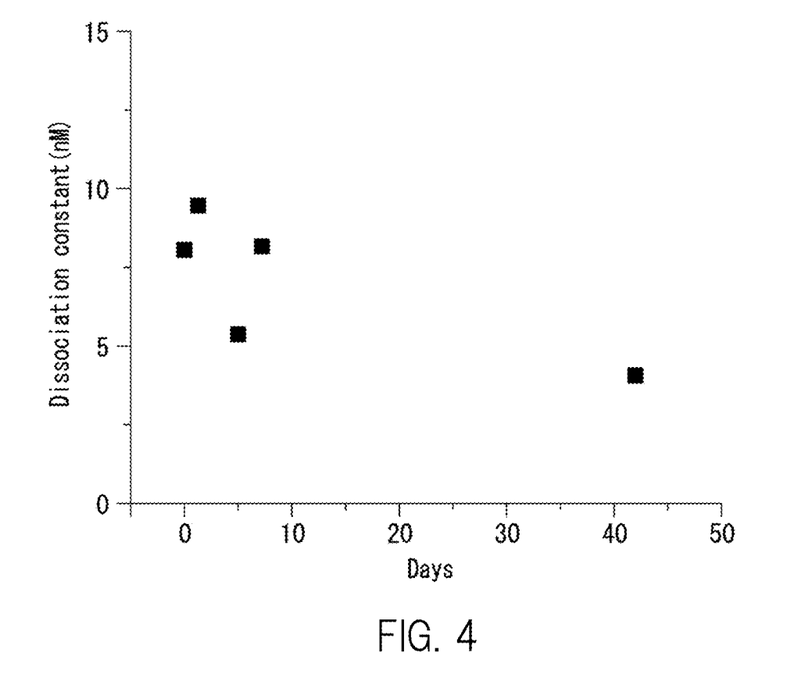
FIG. 4 shows change in bilirubin affinity (dissociation constant, $K_d$ value) of a lyophilized sample stored at room temperature.

After the preparation of the lyophilized samples, in order to investigate how long the activity is maintained, the lyophilized samples that had been dissolved in water were stored at room temperature every few days, and the affinity for bilirubin was measured according to the method described in the above item 7. As a result, it was found that the activity was maintained although the affinity was slightly reduced (FIG. 4).

8. Measurement Using Smartphone

Bilirubin solution at a final concentration of 10 nM, 20 nM, 30 nM, 40 nM, 50 nM, 100 nM, or 250 nM and Coelenterazine-h at a final concentration of 5 μM were mixed with the fusion protein at a final concentration of 50 nM on a 96 multi-well plate, and the resultant mixtures were subjected to measurement using an application (Manual-Custom exposure camera) installed on an iPhone® 6 with ISO set to 1500 and an exposure time set to 0.5 seconds.

Figure 5:
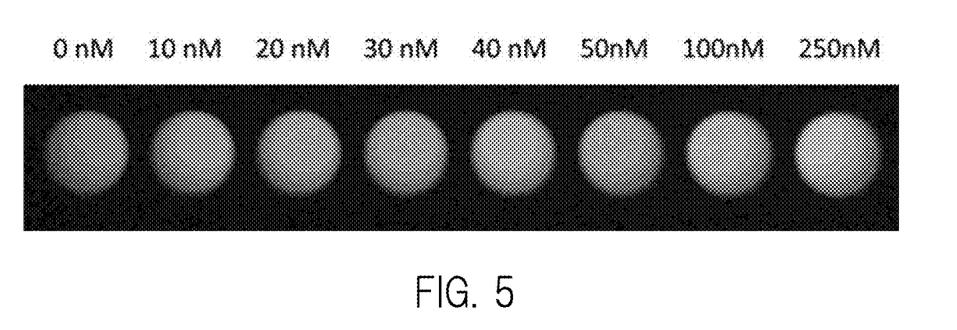
FIG. 5 shows a chemiluminescent image, taken with a smartphone, of solutions containing the wild-type chemiluminescent bilirubin indicator and various concentrations of bilirubin on a 96-well plate.

Color images of the solutions containing the fusion protein and the bilirubin at the various concentrations prepared on the multi-well plate were taken. As a result, the state where the color of the solutions changed from blue to green in a manner dependent on the bilirubin concentration was successfully recorded (FIG. 5). As can be seen in FIG. 5, when the bilirubin concentration was 0 nM, the color of the solution was the luminescent color of the chemiluminescent protein (cyan). As the bilirubin concentration increased, the luminescent color changed toward the luminescent color of UnaG (green). According to an example of the explanation on the state of the color change using RGB, the luminescent colors were as follows: 0 nM (56, 133, 204), 10 nM (79, 157, 215), 20 nM (96, 169, 209), 30 nM (101, 164, 194), 40 nM (119, 179, 189), 50 nM (123, 169, 156), 100 nM (154, 187, 111), and 250 nM (158, 191, 107).

If there is a correlation as shown in FIG. 5, the bilirubin concentration can be calculated from the luminescence data (luminescent color).

Example 2

Figure 6A:
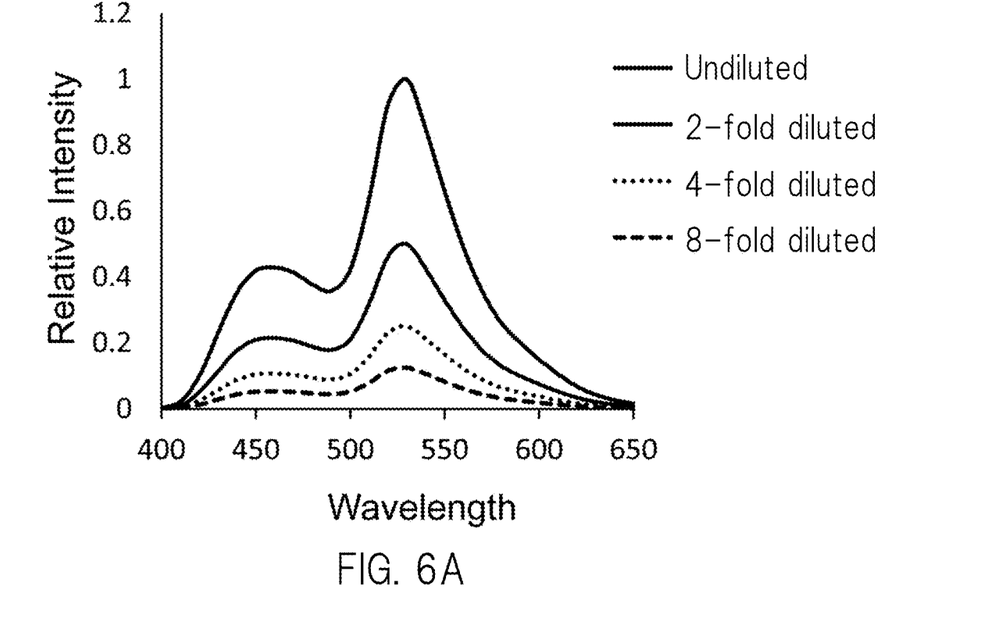
FIG. 6A shows chemiluminescence spectra.
Figure 6B:
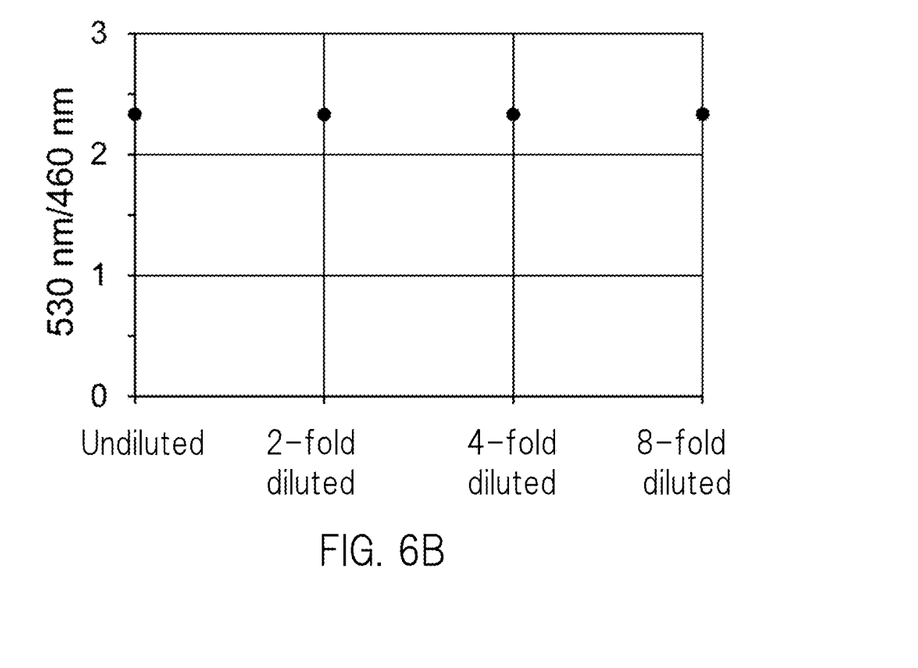
FIG. 6B is a graph showing the relationship between the dilution rate of the UnaG (CΔ0)-NLuc (NΔ1) fusion protein solution (detection reagent) and the ratio value (530 run/460 nm) of peaks obtained from luminescence intensities.

Undiluted, 2-fold diluted, 4-fold diluted, or 8-fold diluted UnaG (CΔ0)-NLuc (NΔ1) fusion protein solution was mixed with bilirubin-luminescent substrate (Coelenterazine-h) solution at a predetermined concentration. Luminescence spectra were measured using a multichannel spectrometer (PMA-12, manufactured by Hamamatsu Photonics K.K.), and from the obtained luminescence intensities, the ratio value (530 nm/460 nm) of the luminescence intensity at a luminescence wavelength of UnaG (530 nm) to the luminescence intensity at the luminescence wavelength of NLuc (460 nm) was calculated. FIGS. 6A and 6B show an example of the result obtained. In FIGS. 6A and 6B, FIG. 6A shows chemiluminescence spectra, and FIG. 6B is a graph showing the relationship between the dilution ratio of the UnaG (CΔ0)-NLuc (NΔ1) fusion protein solution (detection reagent) and the ratio value (530 nm/460 nm).

Comparative Example 1

Figure 7A:
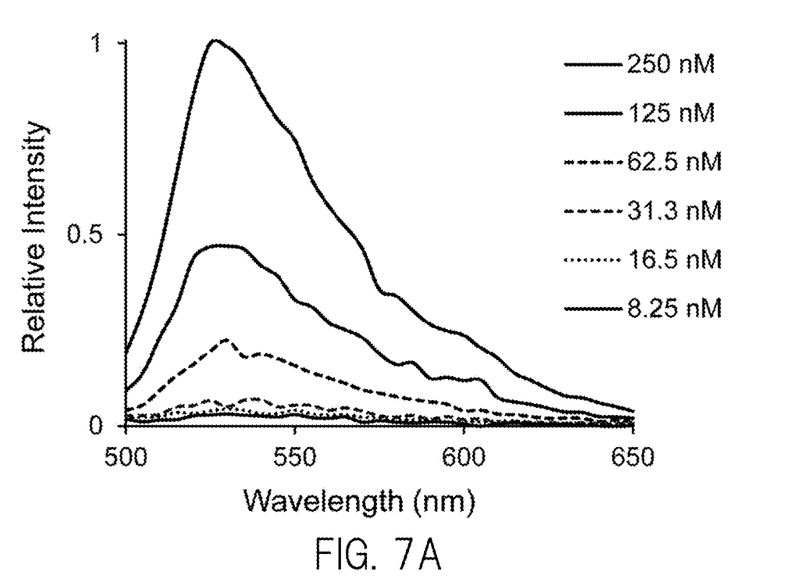
FIG. 7A shows fluorescence spectra.
Figure 7B:
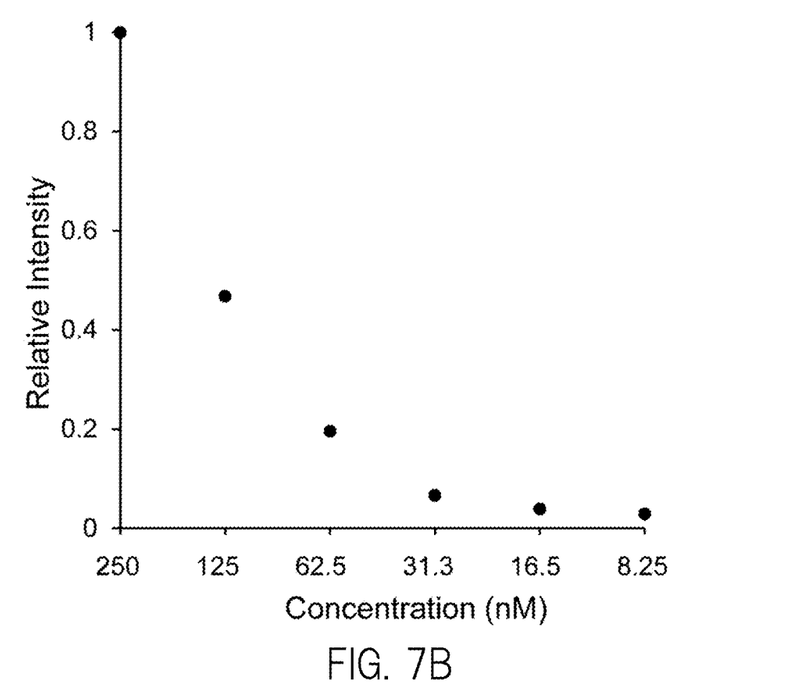
FIG. 7B is a graph showing the relationship between the concentration of a UnaG protein solution (detection reagent) and the fluorescence intensity at the peak (530 nm).

To each well of a 96-well plate (black), 50 μL of UnaG protein solution (8.25 nM, 16.5 nM, 31.5 nM, 62.5 nM, 125 nM, or 250 nM) was added, and then, 50 μL of 400 nM bilirubin solution was added. The 96-well plate was irradiated with excitation light having a wavelength of 450 nm using a microplate reader (SH-9000, manufactured by Corona), and thereafter, fluorescence spectra were obtained. FIGS. 7A and 7B show an example of the result obtained. In FIGS. 7A and 7B, FIG. 7A shows fluorescence spectra, and FIG. 7B is a graph showing the relationship between the concentration of the UnaG protein solution (detection reagent) and the fluorescence intensity at the luminescence wavelength (530 nm) of UnaG.

In Comparative Example 1, as shown in FIGS. 7A and 7B, the fluorescence intensity changed depending on the concentration of the detection reagent in spite of the fact that the concentration of bilirubin to be detected was the same. That is to say, in Comparative Example 1 (a method using a UnaG protein), quantitative measurement cannot be performed.

In contrast, in Example 2 in which the measurement was performed using the UnaG (CΔ0)-NLuc (NΔ1) fusion protein, the waveforms of the spectra were uniform (FIG. 6A) while the luminescence intensity varied depending on the concentration of the detection reagent, and also, as can be seen in FIG. 6B, the peak ratio values (530 nm/460 nm) calculated for the same bilirubin concentrations were substantially the same regardless of the concentration of the detection reagent. Accordingly, it can be said that the UnaG (CΔ0)-NLuc (NΔ1) fusion protein enables measurement that is not affected by the concentration of the detection reagent, i.e., quantitative measurement.

[Sequence Listing Free Text]

SEQ ID NO: 1: Forward primer
SEQ ID NO: 2: Reverse primer
SEQ ID NO: 3: Reverse primer
SEQ ID NO: 4: Reverse primer
SEQ ID NO: 5: Reverse primer
SEQ ID NO: 6: Reverse primer
SEQ ID NO: 7: Forward primer
SEQ ID NO: 8: Forward primer
SEQ ID NO: 9: Forward primer
SEQ ID NO: 10: Reverse primer
SEQ ID NO: 11: Base sequence of UnaG (C 0)-NLuc (N 1) fusion protein
SEQ ID NO: 12: Amino acid sequence of UnaG 0)-NLuc (N 1) fusion protein
SEQ ID NO: 13: Forward primer
SEQ ID NO: 14: Reverse primer
SEQ ID NO: 15: Forward primer
SEQ ID NO: 16: Forward primer
SEQ ID NO: 17: Forward primer
SEQ ID NO: 18: Reverse primer

The invention claimed is:

1. An in vitro method of detecting a biological material in a sample, the method comprising:
   mixing, with the sample, a fusion protein (C) in which a protein (A) capable of binding the biological material and a chemiluminescent protein (B) are fused together and a substrate for the chemiluminescent protein (B); and
   observing a luminescent signal from the sample, wherein the protein (A) and the protein (B) are linked so that resonance energy transfer can occur,
   the protein (A) is either a protein (A1) that can emit fluorescence in a state where the biological material is bound thereto or a protein (A2) that can emit fluorescence on binding an autofluorescent biological material, and
   the protein (B) can excite fluorescence or autofluorescence of the protein (A) with luminescence energy of the protein (B).

2. The method according to claim 1, wherein the protein (A1) is a UnaG protein or a variant thereof, each of which can emit fluorescence in a state where bilirubin is bound thereto, and the biological material to be detected is bilirubin.

3. The method according to claim 1, wherein the protein (A1) is a protein selected from the group consisting of IFP (infrared-fluorescent protein), smURFP (small ultra-red fluorescent protein), and variants thereof, each of which can emit fluorescence in a state where biliverdin is bound thereto, and the biological material to be detected is biliverdin.

4. The method according to claim 1, wherein the protein (A2) is a protein selected from the group consisting of FbFP (flavin mononucleotide (FMN)-based fluorescent protein), iLOV (improved light, oxygen, voltage) proteins, mini-SOG (mini singlet oxygen generator) proteins, and variants thereof, each capable of binding flavin mononucleotide, and the biological material to be detected is flavin mononucleotide.

5. A chemiluminescent indicator comprising:
   a fusion protein (C) in which a protein (A) capable of binding a biological material and a chemiluminescent protein (B) are fused together, wherein the protein (A) and the protein (B) are linked so that resonance energy transfer can occur,
   the protein (A) is a protein (A1) that can emit fluorescence in a state where the biological material is bound thereto,
   the protein (B) can excite fluorescence or autofluorescence of the protein (A) with luminescence energy of the protein (B), and
   the protein (A1) is a UnaG protein or a variant thereof, each of which can emit fluorescence in a state where bilirubin is bound thereto, and
   the biological material to be detected is bilirubin.

6. A vector or transformant that can express the fusion protein (C) defined in claim 5.

7. A method of determining the concentration of a biological material in a sample, the method comprising:
    determining the concentration of the biological material in the sample on the basis of luminescent signal data obtained by the method according to claim 1.

8. The method according to claim 1, wherein the observing a luminescence signal comprises detecting the signal with a color detector.

9. The method according to claim 1, wherein the observing a luminescence signal comprises correlating the luminescence intensity ratio between the protein (A) and the protein (B) in a luminescent signal with the concentration of the biological material.

10. The method according to claim 7, wherein the luminescent signal data comprises the luminescence intensity ratio between the proteins (A) and (B) in the luminescent signal obtained by the method according to claim 1.

11. The method according to claim 8, wherein the color detector is a color camera of a mobile terminal.

12. The method according to claim 1, wherein the protein (B) is NLuc (NanoLuc Luciferase) or variant of NLuc.

13. The method according to claim 1, wherein the sample is a body fluid sample.

14. The method according to claim 1, wherein the sample is whole blood, serum, plasma, or urine.

15. A chemiluminescent indicator comprising:
    a fusion protein (C) in which a protein (A) capable of binding a biological material and a chemiluminescent protein (B) are fused together, wherein the protein (A) and the protein (B) are linked so that resonance energy transfer can occur,
    the protein (A) is a protein (A1) that can emit fluorescence in a state where the biological material is bound thereto, and
    the protein (B) can excite fluorescence or autofluorescence of the protein (A) with luminescence energy of the protein (B), and
    the protein (A1) is a protein selected from the group consisting of IFP (infrared-fluorescent protein) and smURFP (small ultra-red fluorescent protein) or a variant thereof, each of which can emit fluorescence in a state where biliverdin is bound thereto, and
    the biological material to be detected is biliverdin.

16. The chemiluminescent indicator according to claim 15, wherein the protein (B) is NLuc (NanoLuc Luciferase) or variant of NLuc.

17. A vector or transformant that can express the fusion protein (C) defined in claim 15.

18. A chemiluminescent indicator comprising:
    a fusion protein (C) in which a protein (A) capable of binding a biological material and a chemiluminescent protein (B) are fused together, wherein the protein (A) and the protein (B) are linked so that resonance energy transfer can occur,
    the protein (A) is a protein that can emit fluorescence on binding an autofluorescent biological material, and
    the protein (B) can excite fluorescence or autofluorescence of the protein (A) with luminescence energy of the protein (B).

19. The chemiluminescent indicator according to claim 18, wherein the protein (B) is NLuc (NanoLuc Luciferase) or variant of NLuc.

20. A vector or transformant that can express the fusion protein (C) defined in claim 18.

* * * * *

SEQUENCE LISTING

```
<160> NUMBER OF SEQ ID NOS: 18

<210> SEQ ID NO 1
<211> LENGTH: 26
<212> TYPE: DNA
<213> ORGANISM: Artificial Sequence
<220> FEATURE:
<223> OTHER INFORMATION: Forward primer

<400> SEQUENCE: 1
cgcggatccg ggtggttctg gtatgg                                         26

<210> SEQ ID NO 2
<211> LENGTH: 24
<212> TYPE: DNA
<213> ORGANISM: Artificial Sequence
<220> FEATURE:
<223> OTHER INFORMATION: Reverse primer0

<400> SEQUENCE: 2
gctggtacct tccgtcgccc tccg                                           24

<210> SEQ ID NO 3
<211> LENGTH: 24
<212> TYPE: DNA
<213> ORGANISM: Artificial Sequence
<220> FEATURE:
<223> OTHER INFORMATION: Reverse primer1

<400> SEQUENCE: 3
gctggtaccc gtcgccctcc ggta                                           24

<210> SEQ ID NO 4
<211> LENGTH: 24
<212> TYPE: DNA
```

```
<213> ORGANISM: Artificial Sequence
<220> FEATURE:
<223> OTHER INFORMATION: Reverse primer2

<400> SEQUENCE: 4
gctggtaccc gccctccggt agct                                          24

<210> SEQ ID NO 5
<211> LENGTH: 24
<212> TYPE: DNA
<213> ORGANISM: Artificial Sequence
<220> FEATURE:
<223> OTHER INFORMATION: Reverse primer3

<400> SEQUENCE: 5
gctggtaccc ctccggtagc tgcg                                          24

<210> SEQ ID NO 6
<211> LENGTH: 24
<212> TYPE: DNA
<213> ORGANISM: Artificial Sequence
<220> FEATURE:
<223> OTHER INFORMATION: Reverse primer4

<400> SEQUENCE: 6
gctggtaccc cggtagctgc gcac                                          24

<210> SEQ ID NO 7
<211> LENGTH: 31
<212> TYPE: DNA
<213> ORGANISM: Artificial Sequence
<220> FEATURE:
<223> OTHER INFORMATION: Forward primer 1

<400> SEQUENCE: 7
gccggtaccg tcttcacact cgaagatttc g                                  31

<210> SEQ ID NO 8
<211> LENGTH: 30
<212> TYPE: DNA
<213> ORGANISM: Artificial Sequence
<220> FEATURE:
<223> OTHER INFORMATION: Forward primer 2

<400> SEQUENCE: 8
gccggtaccc tcgaagattt cgttggggac                                    30

<210> SEQ ID NO 9
<211> LENGTH: 31
<212> TYPE: DNA
<213> ORGANISM: Artificial Sequence
<220> FEATURE:
<223> OTHER INFORMATION: Forward primer 3

<400> SEQUENCE: 9
gccggtaccg aagatttcgt tggggactgg c                                  31

<210> SEQ ID NO 10
<211> LENGTH: 32
<212> TYPE: DNA
<213> ORGANISM: Artificial Sequence
<220> FEATURE:
<223> OTHER INFORMATION: Reverse primer

<400> SEQUENCE: 10
atgaattctt acgccagaat gcgttcgcac ag                                 32
```

<210> SEQ ID NO 11
<211> LENGTH: 948
<212> TYPE: DNA
<213> ORGANISM: Artificial Sequence
<220> FEATURE:
<223> OTHER INFORMATION: UnaG(C 0)-NLuc(N 1)

<400> SEQUENCE: 11

| | | | | | |
|---|---|---|---|---|---|
| ggtggttctg | gtatggtcga | gaaatttgtt | ggcacctgga | agatcgcaga | cagccataat | 60 |
| tttggtgaat | acctgaaagc | tatcggagcc | ccaaaggaat | taagcgatgg | tggggatgcc | 120 |
| acgacgccga | cattgtacat | ctcccagaag | gacggagaca | aaatgacagt | gaaaatagag | 180 |
| aatggacctc | ctacgttcct | tgacactcaa | gtaaagttca | aattagggga | ggagttcgac | 240 |
| gaatttcctt | ctgatcgaag | aaaaggcgta | aaatctgtcg | tgaacttggt | gggagagaag | 300 |
| ctggtgtacg | tacaaaagtg | ggacggcaag | gagacgacgt | atgtccgaga | gataaaggac | 360 |
| ggtaaactgg | tcgtgacact | tacgatggga | gacgtcgtgg | ctgtgcgcag | ctaccggagg | 420 |
| gcgacggaag | gtaccgtctt | cacactcgaa | gatttcgttg | gggactggcg | acagacagcc | 480 |
| ggctacaacc | tggaccaagt | ccttgaacag | ggaggtgtgt | ccagtttgtt | tcagaatctc | 540 |
| ggggtgtccg | taactccgat | ccaaaggatt | gtcctgagcg | gtgaaaatgg | gctgaagatc | 600 |
| gacatccatg | tcatcatccc | gtatgaaggt | ctgagcggcg | accaaatggg | ccagatcgaa | 660 |
| aaaattttta | aggtggtgta | ccctgtggat | gatcatcact | ttaaggtgat | cctgcactat | 720 |
| ggcacactgg | taatcgacgg | ggttacgccg | aacatgatcg | actatttcgg | acggccgtat | 780 |
| gaaggcatcg | ccgtgttcga | cggcaaaaag | atcactgtaa | cagggaccct | gtggaacggc | 840 |
| aacaaaatta | tcgacgagcg | cctgatcaac | cccgacggct | ccctgctgtt | ccgagtaacc | 900 |
| atcaacggag | tgaccggctg | gcggctgtgc | gaacgcattc | tggcgtaa | | 948 |

<210> SEQ ID NO 12
<211> LENGTH: 313
<212> TYPE: PRT
<213> ORGANISM: Artificial Sequence
<220> FEATURE:
<223> OTHER INFORMATION: UnaG(C 0)-NLuc(N 1)

<400> SEQUENCE: 12

Gly Gly Ser Gly Met Val Glu Lys Phe Val Gly Thr Trp Lys Ile Ala
1               5                   10                  15

Asp Ser His Asn Phe Gly Glu Tyr Leu Lys Ala Ile Gly Ala Pro Lys
            20                  25                  30

Glu Leu Ser Asp Gly Gly Asp Ala Thr Thr Pro Thr Leu Tyr Ile Ser
        35                  40                  45

Gln Lys Asp Gly Asp Lys Met Thr Val Lys Ile Glu Asn Gly Pro Pro
    50                  55                  60

Thr Phe Leu Asp Thr Gln Val Lys Phe Lys Leu Gly Glu Glu Phe Asp
65                  70                  75                  80

Glu Phe Pro Ser Asp Arg Arg Lys Gly Val Lys Ser Val Val Asn Leu
                85                  90                  95

Val Gly Glu Lys Tyr Val Gln Lys Trp Asp Gly Lys Glu Thr Thr Tyr
            100                 105                 110

Val Arg Glu Ile Lys Asp Gly Lys Leu Val Val Thr Leu Thr Met Gly
        115                 120                 125

Asp Val Val Ala Val Arg Ser Tyr Arg Arg Ala Thr Glu Gly Thr Val
    130                 135                 140

```
Phe Thr Leu Glu Asp Phe Val Gly Asp Trp Arg Gln Thr Ala Gly Tyr
145                 150                 155                 160

Asn Leu Asp Gln Val Leu Glu Gln Gly Val Ser Ser Leu Phe Gln
            165                 170                 175

Asn Leu Gly Val Ser Val Thr Pro Ile Gln Arg Ile Val Leu Ser Gly
            180                 185                 190

Glu Asn Gly Leu Lys Ile Asp Ile His Val Ile Pro Tyr Glu Gly
            195                 200                 205

Leu Ser Gly Asp Gln Met Gly Gln Ile Glu Lys Ile Phe Lys Val Val
        210                 215                 220

Tyr Pro Val Asp Asp His His Phe Lys Val Ile Leu His Tyr Gly Thr
225                 230                 235                 240

Leu Val Ile Asp Gly Val Thr Pro Asn Met Ile Asp Tyr Phe Gly Arg
                245                 250                 255

Pro Tyr Glu Gly Ile Ala Val Phe Asp Gly Lys Lys Ile Thr Val Thr
            260                 265                 270

Gly Thr Leu Trp Asn Gly Asn Lys Ile Ile Asp Glu Arg Leu Ile Asn
            275                 280                 285

Pro Asp Gly Ser Leu Leu Phe Arg Val Thr Ile Asn Gly Val Thr Gly
        290                 295                 300

Trp Arg Leu Cys Glu Arg Ile Leu Ala
305                 310

<210> SEQ ID NO 13
<211> LENGTH: 27
<212> TYPE: DNA
<213> ORGANISM: Artificial Sequence
<220> FEATURE:
<223> OTHER INFORMATION: Forward primer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: k is g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (6)..(6)
<223> OTHER INFORMATION: k is g, or t

<400> SEQUENCE: 13
nnknnkgtct tcacactcga agatttc                                    27

<210> SEQ ID NO 14
<211> LENGTH: 22
<212> TYPE: DNA
<213> ORGANISM: Artificial Sequence
<220> FEATURE:
<223> OTHER INFORMATION: Reverse primer

<400> SEQUENCE: 14
ttccgtcgcc ctccggtagc tg                                         22

<210> SEQ ID NO 15
<211> LENGTH: 24
<212> TYPE: DNA
<213> ORGANISM: Artificial Sequence
```

```
<220> FEATURE:
<223> OTHER INFORMATION: Forward primer

<400> SEQUENCE: 15
ggcgtcttca cactcgaaga tttc                                          24

<210> SEQ ID NO 16
<211> LENGTH: 27
<212> TYPE: DNA
<213> ORGANISM: Artificial Sequence
<220> FEATURE:
<223> OTHER INFORMATION: Forward primer

<400> SEQUENCE: 16
ggcggcgtct tcacactcga agatttc                                       27

<210> SEQ ID NO 17
<211> LENGTH: 30
<212> TYPE: DNA
<213> ORGANISM: Artificial Sequence
<220> FEATURE:
<223> OTHER INFORMATION: Forward primer

<400> SEQUENCE: 17
ggcggcagcg tcttcacact cgaagatttc                                    30

<210> SEQ ID NO 18
<211> LENGTH: 19
<212> TYPE: DNA
<213> ORGANISM: Artificial Sequence
<220> FEATURE:
<223> OTHER INFORMATION: Reverse primer

<400> SEQUENCE: 18
ggtaccttcc gtcgccctc                                                19
```